United States Patent
Jeanne et al.

(10) Patent No.: US 10,595,626 B2
(45) Date of Patent: Mar. 24, 2020

(54) METHODS AND SYSTEMS FOR EXTRACTING MOTION CHARACTERISTICS OF A USER TO PROVIDE FEEDBACK TO A USER

(71) Applicant: KONINKLIJKE PHILIPS N.V., Eindhoven (NL)

(72) Inventors: Vincent Jeanne, Bothell, WA (US); Toon Hardeman, S'Hertogenbosch (NL); Arjen Den Hamer, Helmond (NL); Martin John Edwards, Solihull (GB); Jan Wojciech Obrebski, Waalre (NL); Hubert Gerard Jean Joseph Amaury Vroomen, Venray (NL); Alex Merck, Waalre (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 52 days.

(21) Appl. No.: 15/739,064

(22) PCT Filed: Jun. 28, 2016

(86) PCT No.: PCT/EP2016/065005
§ 371 (c)(1),
(2) Date: Dec. 21, 2017

(87) PCT Pub. No.: WO2017/001399
PCT Pub. Date: Jan. 5, 2017

(65) Prior Publication Data
US 2018/0192765 A1    Jul. 12, 2018

Related U.S. Application Data

(60) Provisional application No. 62/185,912, filed on Jun. 29, 2015.

(51) Int. Cl.
*A46B 15/00* (2006.01)
*A61C 17/22* (2006.01)
(Continued)

(52) U.S. Cl.
CPC ...... *A46B 15/0006* (2013.01); *A46B 15/0038* (2013.01); *A61C 17/221* (2013.01);
(Continued)

(58) Field of Classification Search
CPC ............ A46B 15/0006; A46B 15/0038; A61C 17/221
(Continued)

(56) References Cited

U.S. PATENT DOCUMENTS 7,976,388 B2 * 7/2011 Park .................... A46B 15/0002
15/105
8,337,213 B2 * 12/2012 Puurunen ........... A46B 15/0006
434/263
(Continued)

FOREIGN PATENT DOCUMENTS

KR    20100052084 A1    5/2010
WO    WO2006137648 A1    12/2006
(Continued)

OTHER PUBLICATIONS

Viola, P. et al., "Robust Real-Time Face Detection", International Journal of Computer Vision, 57(2), 137-154, 2004.
(Continued)

*Primary Examiner* — Shay Karls

(57) ABSTRACT

Systems and methods for enhancing a user's efficiency while operating an oral hygiene device (10) is provided. In an exemplary embodiment, at least one image is captured using an image capturing component (602), and a region of interest (820) for operating the oral hygiene device is determined based on the at least one captured image. Char-
(Continued)

acteristics corresponding to a motion of the oral hygiene device operated by the user are extracted. An analysis of the extracted characteristics occurs to determine a quality of motion of the oral hygiene device, and feedback is provided to the user to regarding the determined quality of motion of the oral hygiene device.

14 Claims, 14 Drawing Sheets

(51) Int. Cl.
  *G06K 9/46* (2006.01)
  *G09B 19/00* (2006.01)
(52) U.S. Cl.
  CPC ........ *A46B 2200/1066* (2013.01); *G06K 9/46* (2013.01); *G09B 19/0084* (2013.01)
(58) Field of Classification Search
  USPC ................ 15/22.1, 167.1, 105, 106; 434/263
  See application file for complete search history.

(56) References Cited

U.S. PATENT DOCUMENTS

| | | | |
|---|---|---|---|
| 2009/0215015 A1 | 8/2009 | Chu | |
| 2010/0170052 A1* | 7/2010 | Ortins | A46B 15/0002 15/106 |
| 2011/0247156 A1* | 10/2011 | Schmid | A46B 15/0002 15/105 |
| 2014/0065588 A1 | 3/2014 | Jacobson | |

FOREIGN PATENT DOCUMENTS

| | | |
|---|---|---|
| WO | WO2010059484 A1 | 5/2010 |
| WO | WO2010129755 A1 | 11/2010 |
| WO | WO2010144334 A2 | 12/2010 |
| WO | WO2014037856 A1 | 3/2014 |

OTHER PUBLICATIONS

Xiong, X. et al., "Supervised Descent Method and its Applications to Face Alignment", Computer Vision and Pattern Recognition (CVPR), 2013 IEEE Conference, pp. 532-539, IEEE 2013, June.

Osada, R. et al., Matching 3D Models with Shape Distributions:, Shape Modeling and Applications, SMI 2001 International Conference, pp. 154-166, IEEE 2001, May.

Belongie, S. et al., "Shape Matching and Object Recognition using Shape Contexts", IEEE Transactions on Pattern Analysis and Machine Intelligence, 24(4), 509-522, Apr. 2002.

Kazhdan, T. et al., "Symmetry Descriptors and 3D Shape Matching", In Proceedings of the 2004 Eurographics/ACM SIGGRAPH sSmposium on Geometry processing, pp. 115-123, ACM. Jul. 2004.

De Haan G. et al., "True-Motion Estimation with 3-D Recursive Search Block Matching", IEEE Transactions on Circuits and Systems for Video Technology, 3(5), 368-379, Oct. 1993.

Horn, K.P. et al., "Determining Optical Flow", International Society for Optics and Photonics in1981 Technical Symposium East, pp. 319-331, Nov. 1981.

Kalal, Z. et al., "Tracking-Learning-Detection", IEEE Transactions on Pattern Analysis and Machine Intelligence, vol. 6, No. 1, Jan. 2011.

* cited by examiner

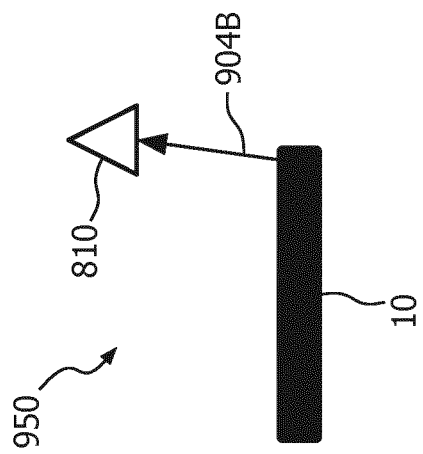
FIG. 11
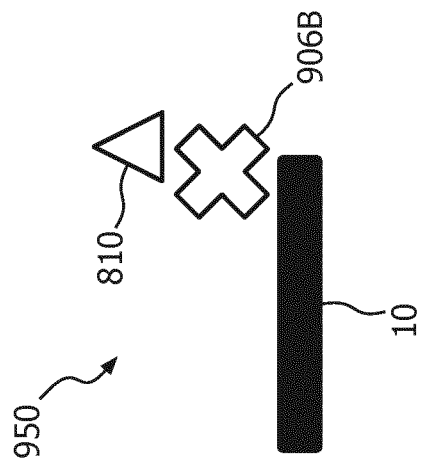
FIG. 12
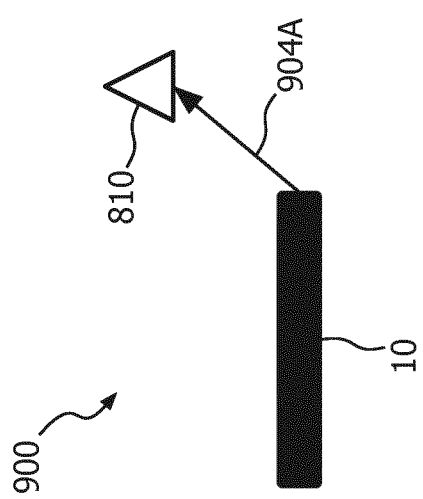
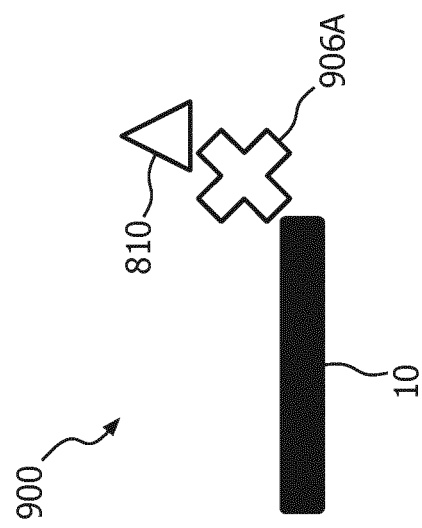

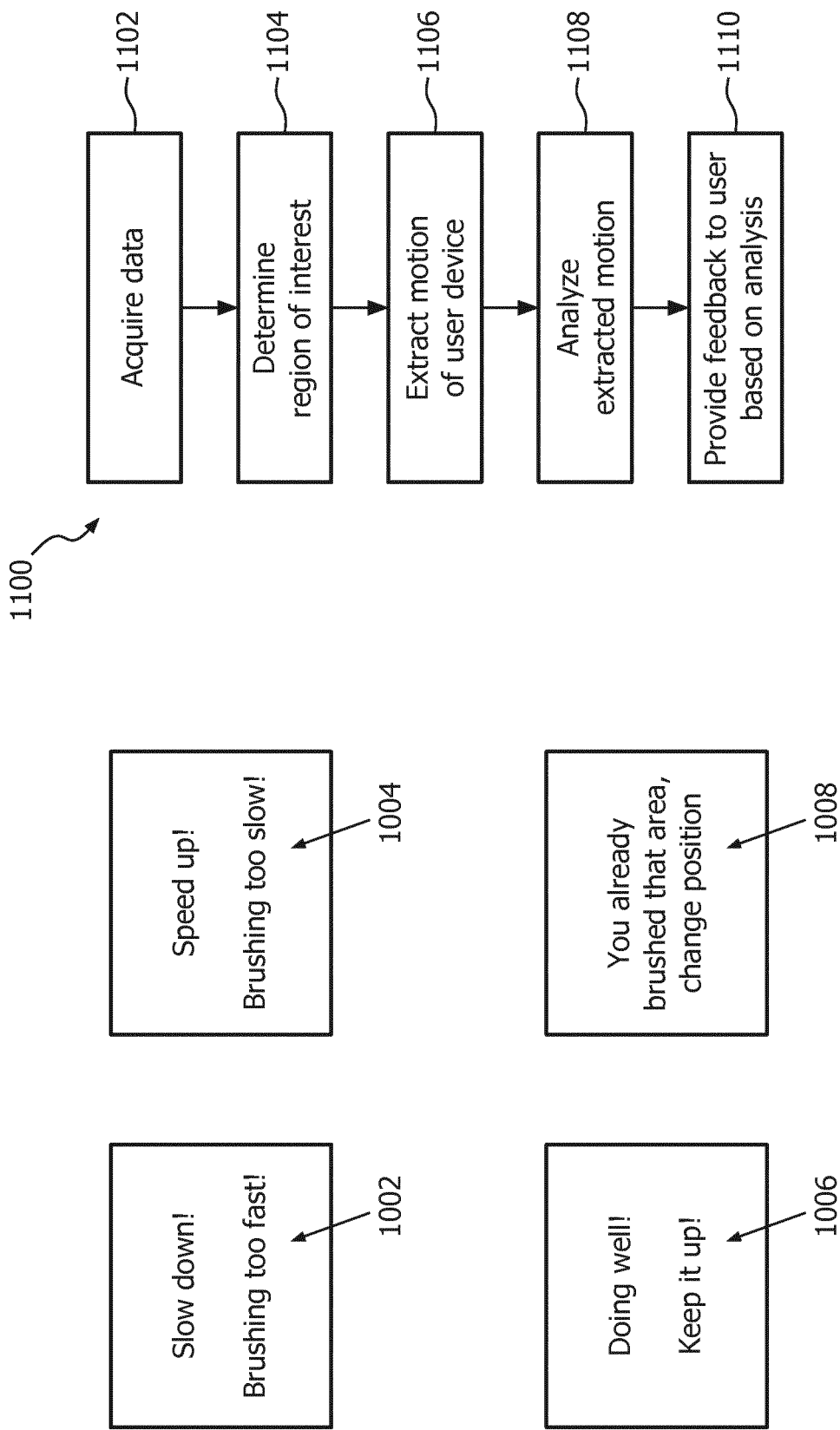

METHODS AND SYSTEMS FOR EXTRACTING MOTION CHARACTERISTICS OF A USER TO PROVIDE FEEDBACK TO A USER

CROSS-REFERENCE TO PRIOR APPLICATIONS

This application is the U.S. National Phase application under 35 U.S.C. § 371 of International Application No. PCT/EP2016/065005, filed on Jun. 28, 2016, which claims the benefit of U.S. Provisional Patent Application No. 62/185,912, filed on Jun. 29, 2015. These applications are hereby incorporated by reference herein.

BACKGROUND OF THE INVENTION

1. Field of the Invention

The present invention generally relates to oral hygiene devices and, in particular, oral hygiene devices including at least one sensor capable of extracting brushing motion characteristics of a user such that feedback is capable of being provided to the user based on the extracted characteristics. The present invention also generally relates to systems and methods for analyzing brushing motion characteristics of a user using a camera based system to extract brushing motion characteristics from captured images and provide feedback to the user based on the extracted characteristics.

2. Description of the Related Art

While correct oral hygiene is important, correcting one's oral hygiene technique is oftentimes difficult. One solution to this problem is for an individual to demonstrate their oral hygiene technique while in the presence of an oral hygiene professional, such as a dentist, and have the oral hygiene professional correct any mistakes performed by the individual. This, however, has inherent flaws because the individual may not remember all of the corrected aspects, as well as the fact that the user may not perform their true oral hygiene technique while in the presence of the oral hygiene professional. Furthermore, over time, the individual's oral hygiene technique may regress to the previous incorrect manner and/or a new incorrect style, or the individual may develop new, incorrect techniques.

One proposed solution to such a problem is to create a "game" where performing correct oral hygiene technique is rewarded by an individual winning the game, whereas incorrect oral hygiene techniques leads to one losing the game. Although this concept may work for children, it is often impractical and ineffective for adults. Furthermore, playing the game may only help one correct their oral hygiene technique while the game is being played, and the individual is not able to see how their overall oral hygiene technique is improving, or when they are deviating too far from a correct technique. Still further, such oral hygiene games are not typically transportable and therefore not capable of providing an individual with real-time feedback regarding the efficacy of their oral hygiene care.

SUMMARY OF THE INVENTION

Accordingly, it is an objective of this invention to provide an oral hygiene device, such as an electronic toothbrush, that is capable of extracting motion characteristic of a user operating the oral hygiene device and providing feedback to the user regarding the efficacy of their technique. This objective is achieved according to the present invention by analyzing motion characteristics of the oral hygiene device and, based on data acquired from at least one sensor included within the oral hygiene device or at least one image capturing component, provide feedback to the user informing them of the efficacy of their operation of the oral hygiene device. Furthermore, it is another object of this invention to provide a user device capable of detecting motion characteristics of a user operating an oral hygiene device. The user device is further operable to extract motion characteristics of the user operating the oral hygiene device, and provide feedback to the user.

In a first exemplary embodiment, a method for providing feedback to a user operating an oral hygiene device including at least one sensor is provided. In one embodiment, data acquired by the at least one sensor of the oral hygiene device is received. The acquired data is then analyzed to determine a quality of motion of the oral hygiene device operated by the user. Feedback is then provided to the user based on the determine quality of motion.

In a second exemplary embodiment, an oral hygiene device is provided. The oral hygiene device, in one embodiment, includes a handle including a power drive system, an attachment assembly, a drive train assembly coupled to the attachment assembly, a magnet operable to produce a magnetic field, at least one sensor mounted within the magnetic field produced by the magnet, and at least one processor. The at least one processor is operable to acquire data from the at least one sensor. The data corresponds to deformations of the magnetic field relative to the at least one sensor, the deformations occurring in response to the attachment assembly having an external force applied thereto while interacting with a region of interest of a user that is operating the oral hygiene device.

In a third exemplary embodiment, a method for enhancing a user's efficacy while operating an oral hygiene device is provided. In one embodiment, at least one image is captured from an image capturing component. A region of interest for operating the oral hygiene device is then determined based on the at least one captured image. Based on the determined region of interest, characteristics corresponding to a motion of the oral hygiene device operated by the user are extracted. The extracted characteristics corresponding to the motion of the oral hygiene device operated by the user are then analyzed to determine a quality of motion of the oral hygiene device. Feedback is then provided to the user regarding the determined quality of motion of the oral hygiene device.

In a fourth exemplary embodiment, a user device for aiding a user in enhancing an effectiveness for operating an oral hygiene device is provided. The user device includes at least one image capturing component, a display screen, communications circuitry, memory, and at least one processor. The at least one processor is operable to capture at least two images of the user operating the oral hygiene device using the at least one image capturing component. In response to detecting that the user is operating the oral hygiene device in a region of interest, motion information of the oral hygiene device is extracted from the at least two captured images. The extracted motion information of the oral hygiene device operated by the user is then analyzed by comparing the extracted motion information to a predefined targeted motion for the oral hygiene device stored in memory on the user device. The comparison determines a quality of the extracted motion of the oral hygiene device. Feedback is then provided to the user operating the oral hygiene device, where the provided feedback includes the quality of the extracted motion information.

BRIEF DESCRIPTION OF THE DRAWINGS

The above and other features of the present invention, its nature and various advantages will be more apparent upon consideration of the following detailed description, taken in conjunction with the accompanying drawings in which:

FIG. 11 is an illustrative diagram describing a change in a location of device 10 based on a change in a position vector between device 10 and a reference object in accordance with various embodiments;

FIG. 12 is an illustrative diagram describing a change in a location of device 10 based on a change in a center of gravity of a captured image in accordance with various embodiments;

FIG. 13 is an illustrative diagram of various user interfaces in accordance with various embodiments; and FIG. 14 is an illustrative flowchart of a process 1100 in accordance with various embodiments.

DETAILED DESCRIPTION OF EXEMPLARY EMBODIMENTS

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise.

Figure 1A:
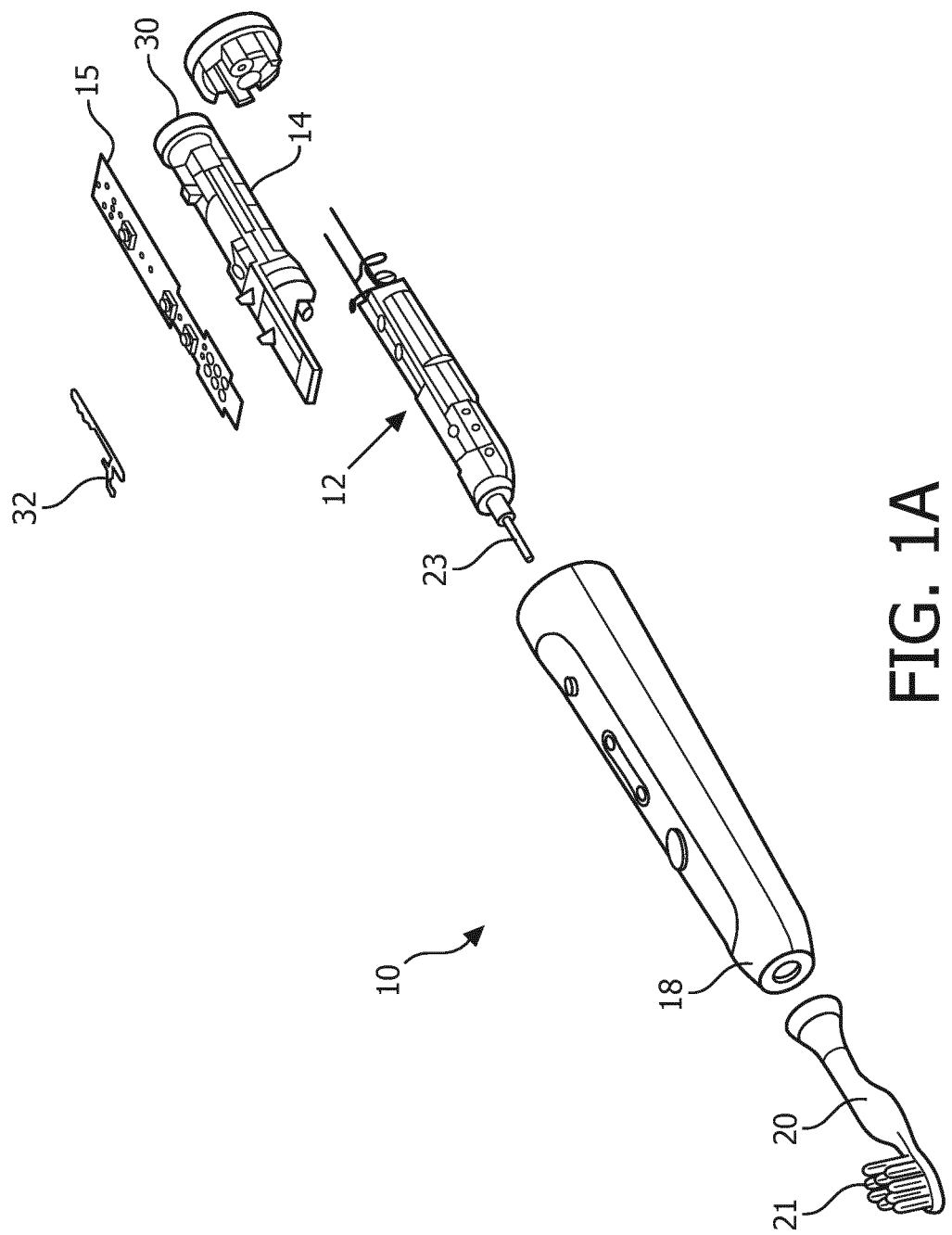
FIG. 1A is an illustrative diagram of an oral hygiene device 10 including at least one sensor in accordance with various embodiments.

FIG. 1A is an illustrative diagram of oral hygiene device 10 including at least one sensor in accordance with various embodiments. Oral hygiene device 10 includes housing 18 containing a drive train assembly 12 resonantly driven by a power system 14 which includes a battery and an electronics carrier (e.g., a printed circuit board or PCB). Oral hygiene device 10 further includes a printed circuit board with a microprocessor control 15 for creating a drive signal for power system 14. Removably secured to a drive stem 23 from the drive train assembly 12 is an attachment assembly 20, at the distal end of which is a brush member 21. At a rear end of drive train assembly 12 is a magnet 30, and mounted within oral hygiene device 10 is also at least one sensor 32. In one exemplary embodiment, at least one sensor 32 is a Hall Effect sensor. A more detailed description of an oral hygiene device including at least one Hall Effect sensor can be found in commonly assigned International Patent Application Publication No. WO 2014/037856, which is incorporated herein by reference in its entirety.

In one embodiment, sensor(s) 32 is a Hall Effect sensor capable of measuring a strength of a magnetic field within housing 18. A magnetic field is capable of being generated by a magnet 30. Application of a Hall Effect sensor in the exemplary embodiment, measures the magnetic field strength relative to the Hall Effect sensor. When an external load, or force, is applied to attachment assembly 20, a deformation of the magnetic field within housing 18 occurs. This deformation is measured via sensor(s) 32, and may provide information regarding an amount of force applied to attachment assembly 20.

In one embodiment, at least one sensor 32 is a force sensor. The force sensor may be included in place of the Hall Effect sensor and/or in conjunction with the Hall Effect sensor. The force sensor allows for information to be extracted from oral hygiene device 10 corresponding to an amount of force applied to attachment assembly 20. In one embodiment, however, the amount of force applied to attachment assembly 20 may also be extracted from a Hall Effect sensor. For example, the force applied to attachment assembly 20 may be obtained, in one embodiment, using the Lorentz Force law.

Figure 1B:
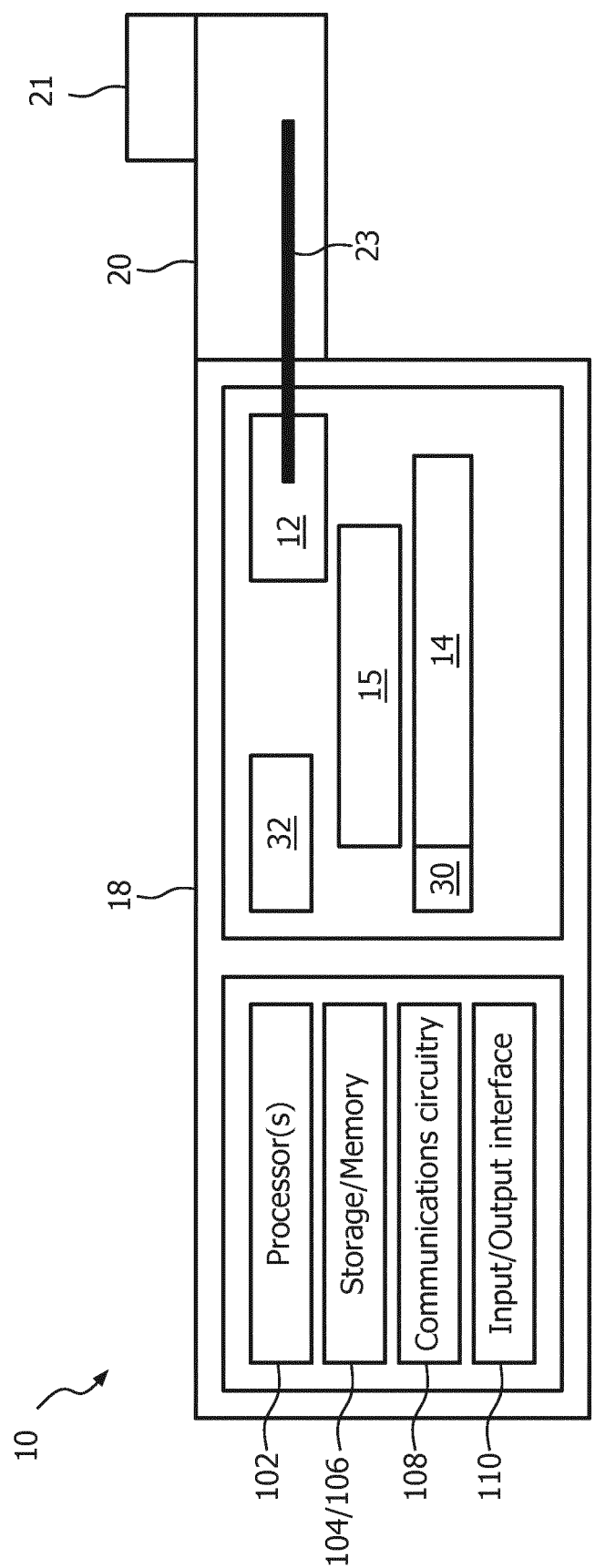
FIG. 1B is an illustrative diagram of an oral hygiene device 10 in accordance with various embodiments.

FIG. 1B is an illustrative diagram of oral hygiene device 10 in accordance with various embodiments. In the illustrated exemplary embodiment oral hygiene device 10 includes additional components located within housing 18.

Oral hygiene device 10, in the illustrated non-limiting embodiment, includes a processor or processors 102, memory 106, communications circuitry 108, and an input/output interface 110. These components may be located on microprocessor control 15, or may be located elsewhere within the housing 18. Processor 102 may include any processing circuitry, such as one or more processors capable of controlling the operations and functionality of oral hygiene device 10. In one embodiment, processor 102 facilitates communications between various components within device 10 (e.g., sensor(s) 32 and communications circuitry 108).

Memory 106, in one embodiment, includes one or more storage mediums. Various types of storage mediums include, but are not limited to, hard-drives, solid state drives, flash memory, permanent memory (e.g., ROM), or any other storage type, or any combination thereof. Any form of data or content may be stored within memory 106, such as photographs, music files, videos, contact information, applications, documents, or any other file, or any combination thereof. Memory 106 also, in one embodiment, includes cache memory, semi-permanent memory (e.g., RAM), or any other memory type, or any combination thereof. In one embodiment, memory 106 may be used in place of and/or in addition to external storage for storing data on oral hygiene device 10.

Communications circuitry 108, in one embodiment, includes any circuitry capable of connecting to a communications network and/or transmitting communications (voice and/or data) to one or more additional user devices and/or servers. Communications circuitry 108 is capable of interfacing with the communications network using any suitable communications protocol including, but not limited to, Wi-Fi (e.g., 802.11 protocol), Bluetooth®, radio frequency systems (e.g., 900 MHz, 1.4 GHz, and 5.6 GHz communications systems), infrared, GSM, GSM plus EDGE, CDMA, quadband, VOIP, or any other protocol, or any combination thereof.

Input/output interface 110, in one embodiment, includes any suitable mechanism or component for receiving inputs from a user operating oral hygiene device 10 and/or generating outputs from a user operating oral hygiene device 10. Input/output interface 110 may include, but is not limited to, an external keyboard, mouse, joystick, or any other suitable input mechanism, or any combination thereof. In one embodiment, input/output interface 110 includes a display capable of displaying a user interface thereon.

Oral hygiene device 10 is operable to acquire data from sensor(s) 32 or any other sensor resident therein, and analyze the data to determine a quality of a brushing motion of the user operating oral hygiene device 10. For example, sensor(s) 32 may be a Hall Effect sensor or a force sensor or both. In one particular example, a Hall Effect sensor may be used to extract force information. As another example, sensor(s) 32 may include one or more accelerometers. In one embodiment, the analyzed data is used to provide feedback to the user via input/output interface 110. For example, input/output interface 110 may include a display screen operable to display a user interface including analysis of the user's quality of brushing. As another example, input/output interface 110 may provide audio, visual, or haptic feedback to the user based on the analyzed data acquired by the at least one sensor 32. Persons of ordinary skill in the art will also recognize that although at least one sensor 32 is used to acquire data, one or more additional sensors may be used.

Figure 1C:
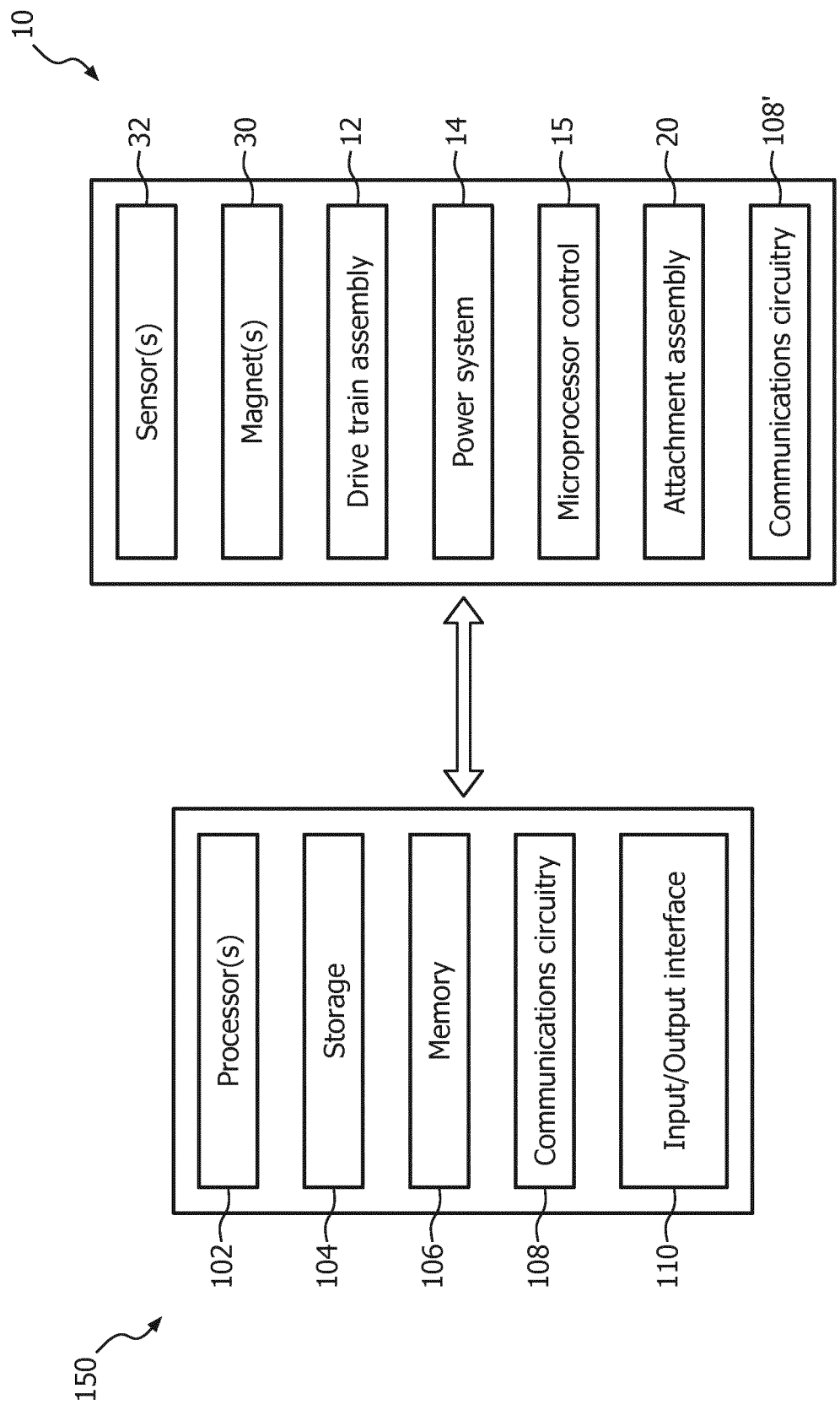
FIG. 1C is an illustrative diagram of oral hygiene device 10 and a user device 150 in accordance with various embodiments.

FIG. 1C is an illustrative diagram of oral hygiene device 10 and user device 150 in accordance with various embodiments. In the illustrated exemplary embodiment, user device 150 includes one or more processors 102, storage 104, memory 106, communications circuitry 108, and input/output interface 110. Oral hygiene device 10, in the illustrated exemplary embodiment, is substantially similar to oral hygiene device 10 of FIG. 1A with the exception that it also include communications circuitry 108', which is substantially similar to communications circuitry 108 of user device 150.

Communications circuitry 108', in one embodiment, enables data acquired by sensor(s) 32 to be transmitted from oral hygiene device 10 to user device 150 via communications circuitry 108. For example, data from sensor(s) 32 (e.g., a Hall Effect sensor) of oral hygiene device 10 may be transmitted to user device 150 via a Wi-Fi connection, a Bluetooth connection, and/or a hardwire connection.

Data acquired by sensor(s) 32 of oral hygiene device 10 corresponds to detected deformations of a magnetic field formed within housing 18 of oral hygiene device 10 based on a user operating oral hygiene device 10. For example, when an external force or load is applied to attachment assembly 20, a deformation may occur to the magnetic field within housing 18 that is measurable by sensor(s) 32. The data is capable of being sent from oral hygiene device 10 to user device 150 for processing, analysis, and/or providing feedback to the user operating oral hygiene device 10. For example, data acquired by sensor(s) 32, such as a Hall Effect sensor, may be analyzed on user device 150 using one or more algorithms stored within memory 106, which determine a quality of the brushing of the user. Feedback is then capable of being provided to the user regarding the determined quality of their brushing motion. In one embodiment, the feedback is displayed on a display screen presenting a user interface.

Persons of ordinary skill in the art will recognize that oral hygiene device 10, 10 may refer to any product able to attend to an individual's oral hygiene, including, but not limited to, electric toothbrushes, non-electric toothbrushes, flossing devices, water jets, tongue cleaners, or any other oral hygiene device, or any combination thereof. Furthermore, in at least one embodiment, oral hygiene device 10, 10 may refer to a personal hygiene device, such as an electronic shaver, hair trimmer, personal groomer, etc., and the foregoing illustrations are not limited to just oral hygiene scenarios.

Figure 2:
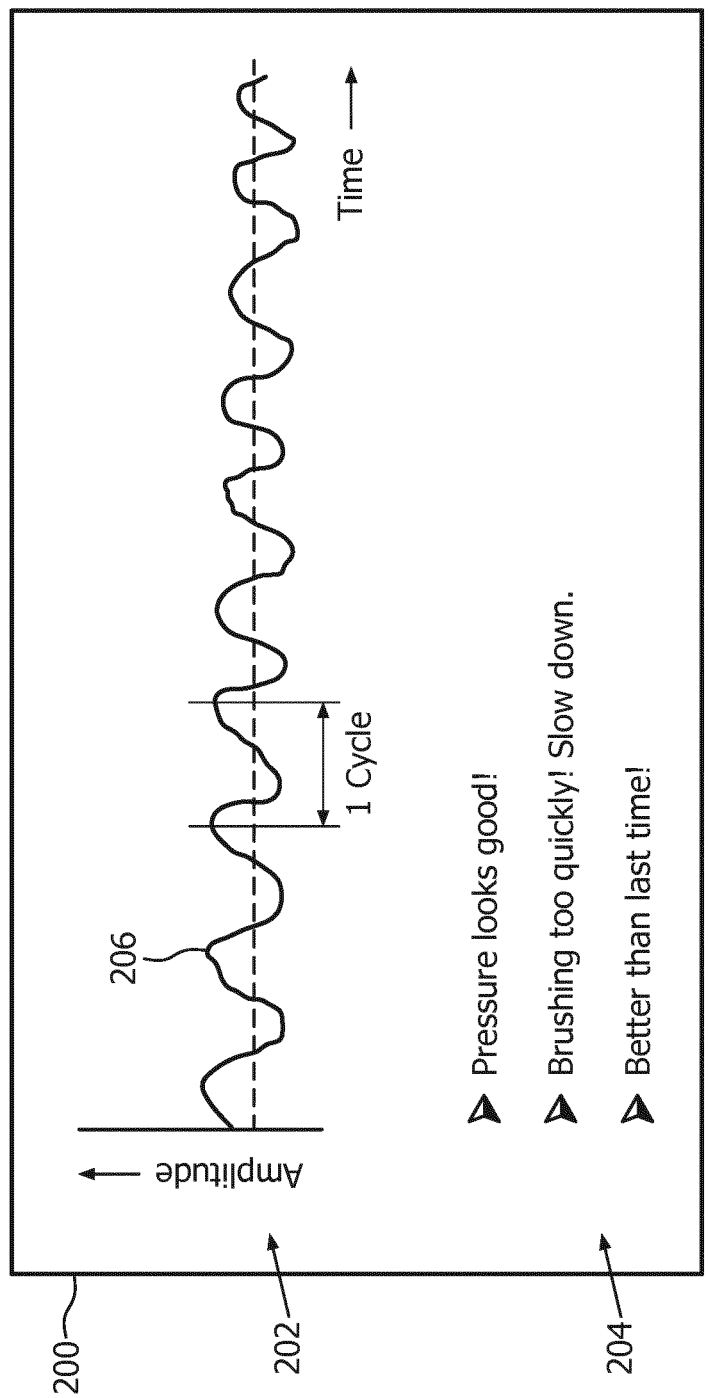
FIG. 2 is an illustrative diagram of a user interface 200 in accordance with various embodiment.

FIG. 2 is an illustrative diagram of a user interface 200 in accordance with various embodiments. User interface 200, in one embodiment, is displayed on a user device including a display screen (e.g., input/output interface 110 of user device 150). For example, user interface 200 may be displayed on a touch-sensitive display screen found on a handheld device such as a smart phone or tablet. As another example, user interface 200 may be displayed on a display screen of an electric toothbrush (e.g., input/output interface 110 of oral hygiene device 10 as shown in FIG. 1B.

User interface 200, in the illustrated embodiment, includes information corresponding to the activity of a user operating oral hygiene device 10 including one or more sensor(s) 32.

In the illustrated embodiment, user interface 200 includes a graph section 202 and a comments section 204. Graph section 202 displays a graphical representation 206 of data obtained from sensor(s) 32 of oral hygiene device 10, and in particular, an amplitude of a brushing motion of oral hygiene device 10 over a period of time that oral hygiene device 10 is in operation. Graph section 202 allows a user operating oral hygiene device 10 to visually see how their brushing technique applies pressure to their teeth over time, and allows a user to correct various inconsistencies that may arise in their technique. For example, if graphical representation 206 has an amplitude that is continually high, low, or generally inconsistent, the user will be able to visually see that information represented within graph section 202 via graphical representation 206. Furthermore, graphical representation 206 enables a user to visualize the frequency of their brushing motion and determine if their brushing technique is too fast or too slow.

Comments section 204, in the illustrative embodiment, includes comments generated by user device 150 displaying on user interface 200 that correspond to the user's brushing technique. For example, if the user is applying a correct amount of pressure to their teeth, a message stating "PRESSURE LOOKS GOOD!" may be displayed on user interface 200, whereas if the user is not applying enough pressure, a message stating "PRESSURE IS TOO LOW" may be displayed on user interface 200. Other comments related to the frequency of the user's brushing and/or the quality of the user's brushing compared to a previous brushing session are also able to be displayed within comments section 204.

In one embodiment, one or more algorithms resident on user device 150 and/or oral hygiene device 10 obtain data from sensor(s) 32 (e.g., a Hall Effect sensor) and convert that data into a numerical representation. The numerical representation may then be compared to a predefined value for brushing pressure, frequency, and/or quality, which are operable to cause one or more different messages to appear in comments section 204. For example, a look-up table may be included in memory 106 on user device 150 and/or oral hygiene device 10 that informs user device 150 and/or oral hygiene device 10 to display the message "PRESSURE LOOKS GOOD!" in the comments section 204 of user interface 200 when the obtained data from sensor(s) 32 indicates that a correct amount of pressure is being applied by the user operating oral hygiene device 10.

Figure 3B:
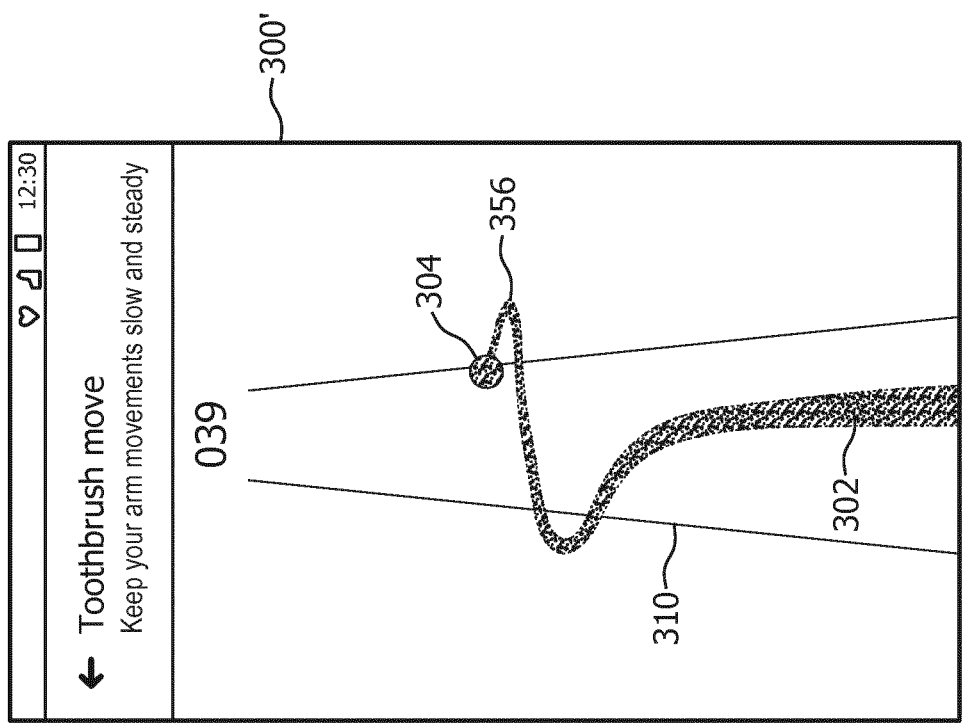
FIGS. 3A and 3B are illustrative diagrams of user interfaces 300 and 300', respectively, in accordance with various embodiments.
Figure 3A:
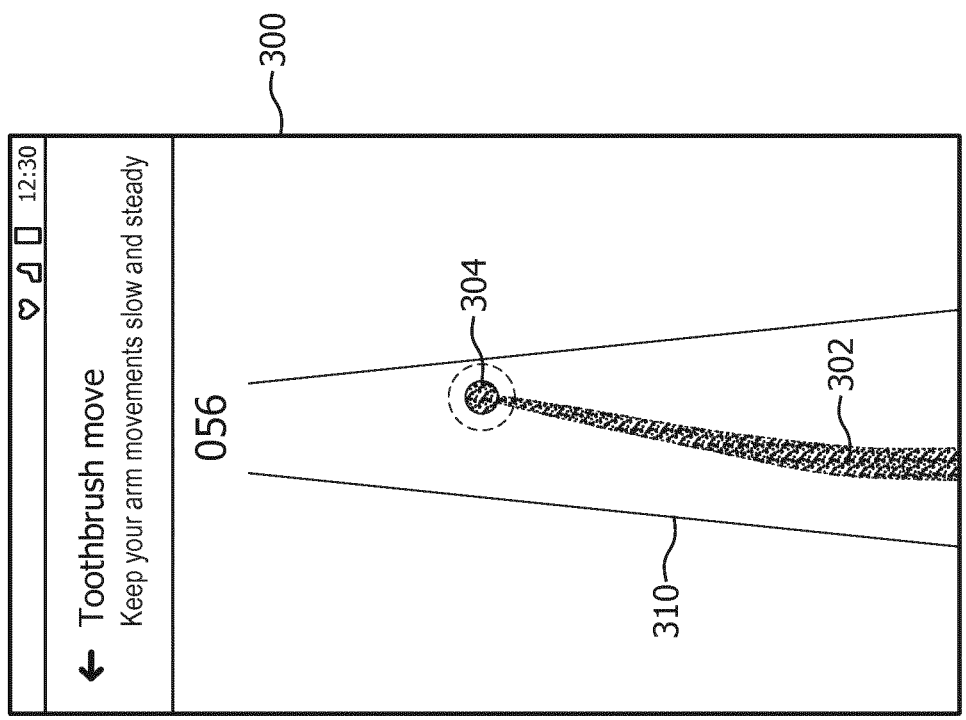

FIGS. 3A and 3B are illustrative diagrams of other user interfaces 300 and 300', respectively, in accordance with various embodiments. In the illustrative embodiments, user interface 300 displays graphics that inform a user when their brushing motion is below a targeted brushing motion, whereas user interface 300' displays graphics that inform a user when their brushing motion is greater than the targeted brushing motion. User interfaces 300, 300' are capable of being displayed on a display screen of a user device that receives data obtained by sensor(s) 32 of oral hygiene device 10, and/or a display screen located on oral hygiene device 10 and/or user device 150.

In one embodiment, the targeted brushing motion is stored in memory 106 on user device 150 and/or oral hygiene device 10, which display user interface 300. The targeted brushing motion may be defined prior to any brushing activity occurring. For example, the targeted brushing motion may be defined by the user, the user's parents, and/or the user's oral hygiene professional. As the user brushes their teeth, sensor(s) 32 of oral hygiene device 10 acquire data related to an external force applied to oral hygiene device 10. For example, if sensor(s) 32 is a Hall Effect sensor, the external force applied will cause an internal deformation of the magnetic field within housing 18 of oral hygiene device 10 and the internal deformation is measured relative to sensor(s) 32 (e.g., a Hall Effect sensor) of oral hygiene device 10. The Hall Effect sensor, in one embodiment, is set to have a data acquisition rate at least twice of an expected maximum motion frequency, however persons of ordinary skill in the art will recognize that any suitable acquisition rate may be used and the aforementioned is merely exemplary.

User interface 300 includes a target brushing motion window 310 that indicates bounds of the targeted brushing motion for the user operating oral hygiene device 10. The user's current brushing motion is indicated, in one embodiment, by a marker 304. As the brushing motion changes over time, a path 302 is displayed that indicates the various positions of marker 304 during brushing. In one embodiment, 300, marker 304 and path 302 indicate that the user's brushing motion is lower than the targeted brushing motion defined by target brushing motion window 310. The user may be capable of visually seeing user interface 300 presented on a display screen (e.g., input/output interface 110) and appropriately correcting their brushing technique. For example, marker 304 and path 302 of user interface 300 may indicate that the brushing motion of the user is lower than the targeted brushing motion, and therefore the user may increase their brushing motion (e.g., frequency and/or amplitude).

In user interface 300', the brushing motion of the user is greater than the target brushing motion. As seen in FIG. 3B, path 302 shows that the user, at a point 356, has exceeded the target brushing motion defined by target brushing motion window 310. In this particular scenario, the user is able to view user interface 300' and correct their brushing by decreasing their frequency and/or amplitude of brushing to return to the target brushing motion.

Figure 4:
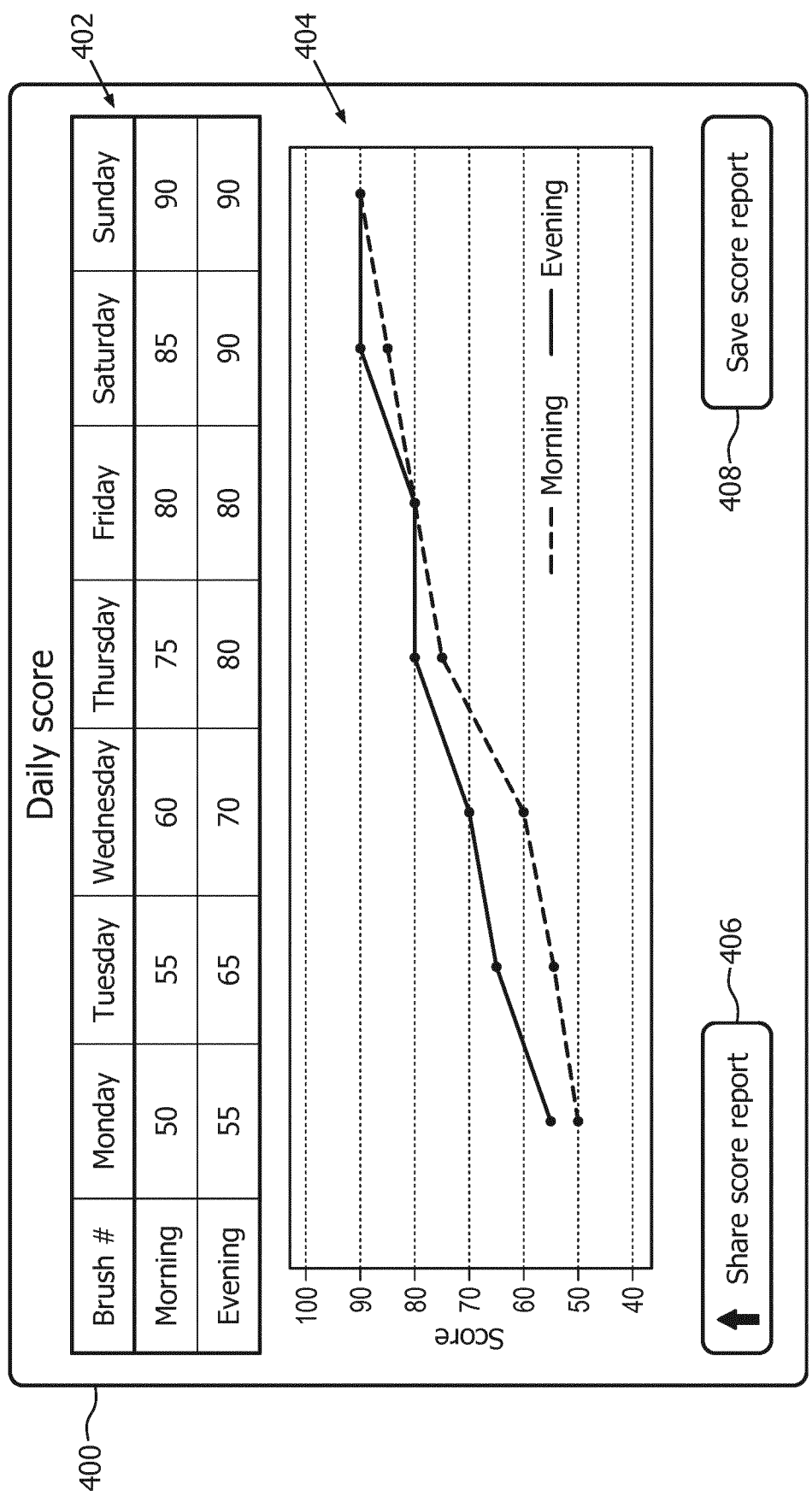
FIG. 4 is an illustrative diagram of a user interface 400 in accordance with various embodiments.

FIG. 4 is an illustrative diagram of another user interface 400 in accordance with various embodiments. User interface 400, in one embodiment, is displayed on a display screen (e.g., input/output interface 110). In one embodiment, user interface 400 includes a scoring information chart 402 that details a user's brushing score each time the user brushes their teeth. For example, a score may be given to each brushing session, where the higher the score, the better the brushing session, and the lower the score, the worse the brushing session.

In one exemplary embodiment, scoring information chart 402 includes a morning score and an evening score for each day of one week. Persons of ordinary skill in the art will recognize that although only seven (7) days and two sessions per day are displayed, any number of days and any number of sessions may be included within scoring information chart 402. A scoring information graph 404 is displayed within user interface 400, in one embodiment, that tracks the user's brushing score graphically so that the user visualizes whether or not their brushing technique is improving from day to day. This may be especially useful for parents to use with their children to ensure that they are continually brushing their teeth and that they are learning proper oral hygiene care and not repeating the same incorrect brushing techniques.

User interface 400 also includes, in the illustrative embodiment, a share score report button 406 and a save score report button 408. Share score report button 406 allows data included within scoring information chart 402 and/or scoring information graph 404 to be shared with one or more contacts, social media websites, and/or user devices. For example, a user particularly proud of their score for a certain week may share their scoring information with their family member or friends. As another example, a user may share their scoring information with their dental professional to inform them of their diligent care.

Save score report button 408, in one embodiment, allows a user to store their score(s) on their user device 150. For example, a user may store each score from week to week on their user device so that a robust data set may be produced to review with their dental professional at their next appointment. The saved scoring information may be stored in a memory on a user device 150 and/or on a cloud storage system with which the user has an account on or which may be accessed by other individuals (e.g., parents, dental professionals, etc.).

Figure 5:
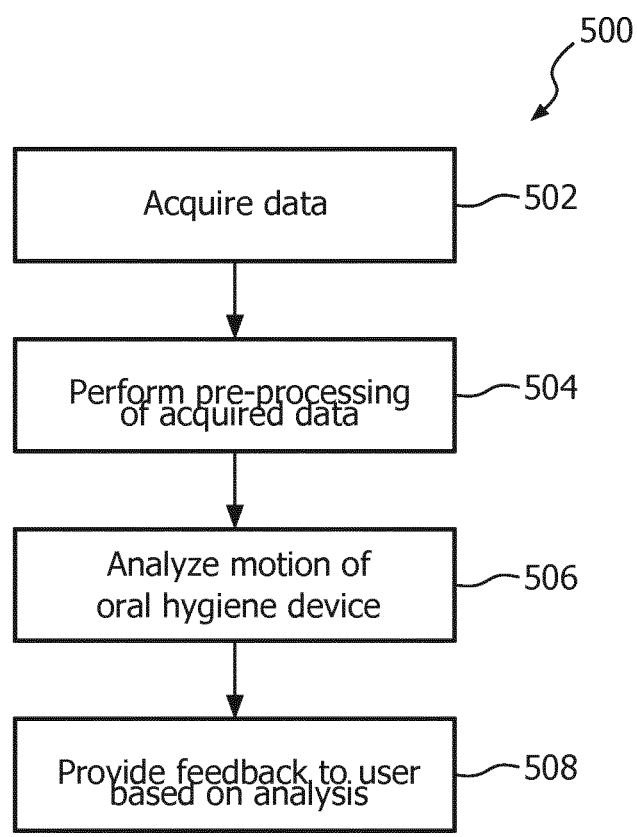
FIG. 5 is an illustrative flowcharts of a process 500 in accordance with various embodiments.

FIG. 5A i an illustrative flowchart of process 500 for providing feedback to a user operating oral hygiene device 10 in accordance with various embodiments. Process 500 begins at step 502. At step 502, data is acquired, in one embodiment, from sensor(s) 32 of oral hygiene device 10. For example, data may be acquired from a Hall Effect sensor located on oral hygiene device 10. In another embodiment, data is acquired from one or more additional sensors located on oral hygiene device, such as a force sensor and/or a combination of a force sensor, a Hall Effect sensor, and/or an accelerometer. In some embodiments, that date may be transmitted to user device 150 via communications circuitry 108 and 108'. Various ways that the data is transferable from oral hygiene device 10 to user device 150 include, but are not limited to, Bluetooth®, Wi-Fi, cellular data, and/or a wired connection.

In one embodiment, sensor(s) 32 is set to have an acquisition rate at least twice an expected maximum motion frequency. The motion frequency typically ranges between 0.1 Hz and 8 Hz. If the motion frequency is 0.1 Hz, then the acquisition rate should be at least 0.2 Hz, whereas if the motion frequency is 8 Hz, then the acquisition rate should be at least 16 Hz, for example. In one particular embodiment, the acquisition rate is set to be approximately 30 Hz. However, persons of ordinary skill in the art will recognize that any acquisition rate may be set for any maximum motion frequency, and the aforementioned is merely exemplary.

At step 504, pre-processing of the acquired data is performed by one or more algorithms stored in memory 106 by processor(s) 102 of oral hygiene device 10 and/or user device 150. Pre-processing the acquired data allows, in one embodiment, the data to be modified so that it can be more readily analyzed. In one embodiment, pre-processing of the acquired data corresponds to downscaling or subsampling the acquired data. In another embodiment, data reduction is performed on the acquired data to emphasize the brushing motion information. For example, Empirical Mode Decomposition ("EMD") may be performed on the acquired data to turn raw brushing motion signals to create a collection of Intrinsic Mode Function ("IMF") data, which highlights the extrema and/or zero-crossings of the brushing force information. In yet another embodiment, pre-processing of the acquired data corresponds to application of a band-pass filter to remove noise/irrelevant frequency information. For example, a 4 Hz low-pass filter may be applied that removes all frequency information exceeding 4 Hz. Persons of ordinary skill in the art will recognize that, in one embodiment, pre-processing of the acquired data may not be required because the data, as initially acquired, may already be in a suitable format.

At step 506, the brushing motion of oral hygiene device 10 is analyzed based on the pre-processed acquired data. In one embodiment, the analysis is performed by processor 102 of oral hygiene device 100 and is based on one or more algorithms stored in memory 106 of oral hygiene device 10. In another embodiment, the analysis is performed by processor 102 of user device 150, and is based on one or more algorithms stored in memory 106 of user device 150. User device 150, for example, may correspond to a smartphone or tablet, and therefore may include greater processing capabilities than oral hygiene device 10. The one or more algorithms are operable to decompose the acquired data's analyzable features, such as, for example, brushing motion frequency and/or brushing motion amplitude.

The brushing motion frequency, in one embodiment, is extracted using Fourier analysis to detect a dominant motion frequency using maximum amplitude detection. For example, motion components are windowed using a Hanning window and then sent to a Fast Fourier Transform ("FFT"), to extract dominant frequencies by an index of the maximal frequency amplitude. As another example, a Hilbert transformation may be used for substantially instantaneous frequency estimation.

In another exemplary embodiment, the brushing motion frequency is determined by extracting extrema or a number of zero-crossing in the motion components. Akin to frequency estimation, assuming that a dominant frequency carrier in the obtained signal is in fact the frequency of interest, extraction of the extrema and/or zero-crossings enables the overall system to correlate with expert assessment.

In still another exemplary embodiment, a three-band-pass filter is used. The three-band-pass filter is capable of being implemented in software resident on oral hygiene device 10 or user device 150, for example. The three band-pass filter operates to compute an amount of energy as a Root Means Square ("RMS") value in an upper and lower band of the three bands, relative to an amount of energy in a middle band, to indicate a dominant brushing frequency. For example, after the signal is obtained and translated into the frequency domain, an amount of energy in each band of the three bands is determined. If a first, second, and third band go from 0.5-1.5 Hz, 1.5-2.5 Hz, and from 2.5 Hz and higher, respectively, the energy values for each band are extracted, and the band including the dominant amount of energy is determined. Whichever band includes the dominant amount of energy will reveal the region including the dominant frequency.

The brushing motion amplitude, in one embodiment, is obtained by determining a distance between consecutive extrema of the motion signals. For example, the distance between two consecutive extrema may correspond to an amount of time transpiring between two maximum, or minimum, motion signals. The motion signals may change in amplitude over time, therefore the distance between consecutive extrema may be referred to as a temporal distance or a time between consecutive extrema. In another embodiment, the brushing motion amplitude is extracted based on the amplitude of the dominant frequency in the Fourier representation of the obtained signals. As still yet another embodiment, the brushing motion amplitude is obtained by enveloping about the motion components.

In one exemplary embodiment, additional features of the brushing motion are analyzed based on the brushing motion frequency and brushing motion amplitude extracted. Derivatives of the signal may be used to obtain various characteristics of the user's brushing pattern. For example, a first order derivative of the brushing signal will yield velocity readings corresponding to the user's motion. This data is capable of being used to determine how quickly a user is moving oral hygiene device 10 from tooth to tooth, for example. As another example, a second order derivative of the brushing signal will yield acceleration readings corresponding to the user's brushing motion.

At step 508, feedback is provided to a user operating oral hygiene device 10, where the feedback is based, in one embodiment, on the analysis of the user's brushing motion. In one embodiment, the provided feedback corresponds to information displayed by means of a user interface, such as user interfaces 200, 300, 350, and/or 400 on oral hygiene device 10 and/or user device 150. The information displayed therein may inform the user of a quality of their brushing motion. For example, display screens 300 and 350 indicate how well a user is adhering to a predefined brushing motion by informing the user when they are brushing below a target brushing motion or above a target brushing motion. As another example, user interface 200 indicates a user's brushing motion amplitude and/or frequency, as well as informative messages letting the user know how their current brushing motion relates to a predefined target brushing motion.

In one embodiment, audio, visual, and/or haptic feedback is provided to the user based on the analysis of their brushing motion. For example, if the user is applying more pressure than they should be, oral hygiene device 10 and/or user device 150 may provide a vibration, an audio signal (e.g., a beep), and or a visual signal (e.g., a flashing light) informing the user that their brushing motion is incorrect.

In one embodiment, the size of oral hygiene device 10 dictates which type of feedback is provided to the user. For example, if a user device 150 is not used, and oral hygiene device 10 is too small to include a display screen, or oriented such that while brushing, the user is not capable of viewing a display screen, visual feedback may be difficult or ineffective. In this particular scenario, an audio signal or haptic response may be more suitable. However persons of ordinary skill in the art will recognize that any type of feedback may be provided to the user in any suitable manner, and the aforementioned are merely exemplary. For example, a display screen on user device 150 may display user interface 300 or 350, which may indicate to a user operating oral hygiene device 10 that their brushing motion is too low or too high, while at the same time an audio signal may be generated by oral hygiene device 10 to signify the incorrect brushing technique of the user.

Figure 6:
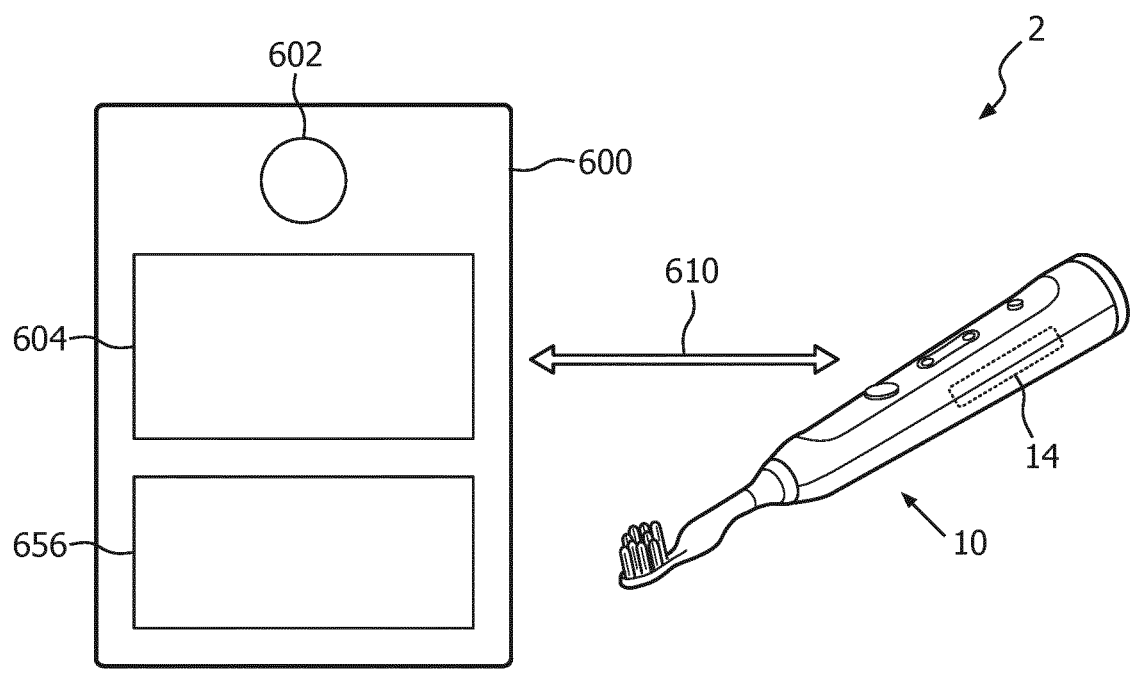
FIG. 6 is an illustrative diagram of a system 2 including a user device 150 and oral hygiene device 10 in accordance with various embodiments.

FIG. 6 is an illustrative diagram of system 2 including a user device 150 and oral hygiene device 10 in accordance with various embodiments. User device 150 of system 2, in one illustrative non-limiting embodiment, includes a camera 602 and a display screen 604. For example, user device 150 may correspond to a user's smart phone or tablet, which may include software resident thereon to analyze a user's brushing motion while they operate oral hygiene device 10. A motion of a user operating oral hygiene device 10, in one embodiment, is capable of being viewed/monitored by camera 602 of user device 150 for analysis, as well as providing feedback to the user operating oral hygiene device 10, which is explained in greater detail below. In one embodiment, user device 150 and oral hygiene device 10 are operable to couple with one another via connection means 610. Connection means 610 includes any wireless or wired connection including, but not limited to, Bluetooth®, Wi-Fi, cellular (e.g., LTE), and/or hardwire connections. In one embodiment, connection means 610 enables feedback to be provided from user device 150 to oral hygiene device 10, or vice versa. In another embodiment, user device 150 further includes one or more additional components such as processing circuitry, feedback circuitry, and/or charging circuitry. In one embodiment, user device 150 includes charging circuitry 656 to that is capable of charging power system 14 of oral hygiene device 10. For example, user device 150 may be a base station compatible with oral hygiene device 10.

Figure 7:
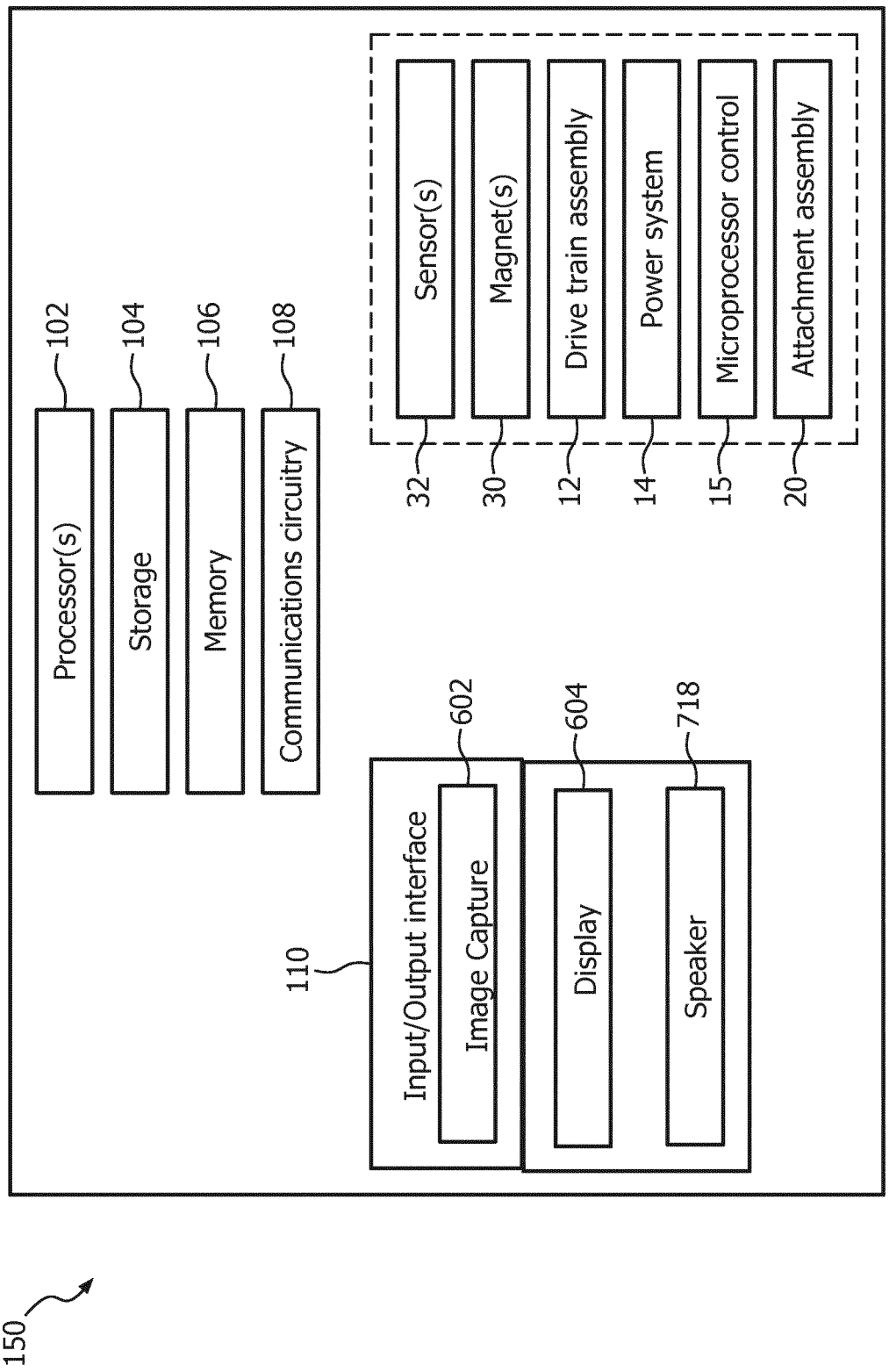
FIG. 7 is an illustrative block diagram of a user device 150 in accordance with various embodiments.

FIG. 7 is an illustrative block diagram of user device 150 in accordance with various embodiments. User device 150 may be a smartphone or tablet, or may be a base station for an oral hygiene device 10. In yet another exemplary embodiment, user device 150 also includes one or more cameras 602 for capturing images and/or videos.

User device 150, in the illustrative exemplary embodiment, includes one or more processors 102, storage 104, memory 106, communications circuitry 108, and input/output interface 110. Camera 602, in one exemplary embodiment, corresponds to any image capturing component capable of capturing images and/or videos. For example, camera 602 may capture photographs, sequences of photographs, rapid shots, videos, 3D images/videos, or any other image type, or any combination thereof.

Input/output interface 110, in the illustrative embodiment, may also include a display 604 and a speaker 718, or any other suitable mechanism or component for generating outputs. Display 604, in one embodiment, corresponds to any type of display capable of presenting content to a user and/or on user device 150. Display 604 is capable of being any size and located on one or more regions/sides of user device 150. For example, display 604 may fully occupy a first side of user device 150, or may occupy only a portion of the first side. Various display types include, but are not limited to, liquid crystal displays ("LCD"), monochrome displays, color graphics adapter ("CGA") displays, enhanced graphics adapter ("EGA") displays, variable graphics array ("VGA") displays, or any other display type, or any combination thereof. In one embodiment, display 604 is a touch screen and/or an interactive display. In another embodiment, the touch screen includes a multi-touch panel coupled to processor(s) 102 of user device 150. In still another embodiment, display 604 is a touch screen including capacitive sensing panels.

Speaker 718, in one embodiment, corresponds to any suitable mechanism for outputting audio signals. For example, speaker 718 may include one or more speaker units, transducers, or array of speakers and/or transducers capable of broadcasting audio signals and audio content to a user interfacing with user device 150. In one embodiment, speaker 718 corresponds to headphones or ear buds capable of broadcasting audio directly to a user operating user device 150.

In one exemplary embodiment, user device 150 includes one or more components of oral hygiene device 10 of FIG. 1A. For example, user device 150 may include sensor(s) 32, magnet(s) 30, drive train assembly 12, power system 14, microprocessor control 15, and attachment assembly 20. Persons of ordinary skill in the art will recognize that although user device 150 includes one or more features of oral hygiene device 10, any number of additional components may be added, or any number of components may be removed, and the aforementioned description is merely exemplary. Furthermore, user device 150, in one embodiment, is substantially similar to oral hygiene device 10 of FIG. 1B with the exception that the former includes one or more of cameras 602, display 604, and/or speaker 718.

In one exemplary embodiment, user device 150 corresponds to oral hygiene device 10, with the exception that the former includes camera 602 embedded therein. In one embodiment, camera 602 may be external such that it protrudes from housing 18 of oral hygiene device 10 to capture images of attachment assembly 20 (e.g., the brush member 21) while interacting with the user's teeth. In another embodiment, camera 602 is embedded in attachment assembly 20. In this particular scenario, camera 602 may include one or more lights (e.g., LEDs, infrared) to illuminate a portion of the user's mouth that will be interacted with. Various landmarks within a user's mouth may then be used as a reference point to determine motion and/or quality of brushing activity. For example, a user's tongue, palate, and/or palatine uvula may be used as a "landmark" to determine where in the user's mouth oral hygiene device 10 is located. Motion is capable of being determined, in one embodiment, based on changes in captured images between one image and a subsequent image based on differences between the two images, such as differences in position of a tooth or teeth with respect to the physical landmark.

Figure 8:
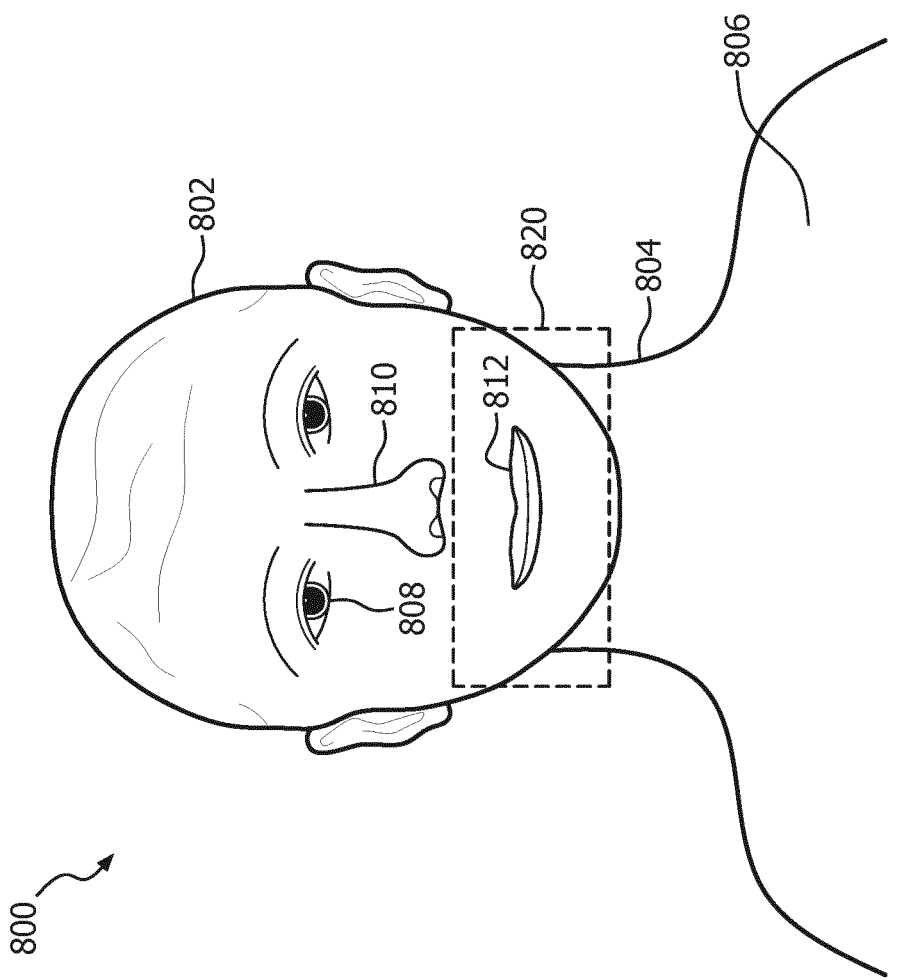
FIG. 8 is an illustrative diagram of an image 800 of a user in accordance with various embodiments.

FIG. 8 is an illustrative diagram of image 800 of a user in accordance with various embodiments. Image 800 includes a face 802, a neck 804, and a torso 806 of the user. Head 802 includes eyes 808, nose 810, and mouth 812. In one embodiment, one or more additional features may be included to describe the user including, but not limited to, ears, eyebrows, chins, cheeks, hair, and/or nostrils.

In one embodiment, a region of interest 820 is included within image 800 of the user. In one embodiment, region of interest 820 corresponds to a relevant portion of the user where motion corresponding to the user operating oral hygiene device 10 will occur, such as is shown in FIG. 9. For example, region of interest 820 may, when the user is brushing their teeth, correspond to a region surrounding mouth 812. As another example, if the user is shaving, region of interest 820 may be slightly larger such that portions of the user's face 802 where one may shave are included.

In one embodiment, region of interest 820 may be predefined by the user. For example, a user may manually draw an outline of region of interest 820 on a user interface displayed on display screen 604 of user device 150. As another example, the user may be presented with region of interest 820 approximated by user device 150, and the user may manually adjust the borders of region of interest 820 such that they more appropriately conform with the user's facial structure.

In one embodiment, region of interest 820 is determined based on detection of one or more facial or body features of the user by user device 150. In one exemplary embodiment, detection of the user's face 802 and torso 806 are performed using any suitable face detector. For example, a Viola-Jones object detection framework may be used to detect region of interest 820 within image 800. In one embodiment, consecutive images captured by camera 602 of user device 150 have a Viola-Jones face detector used to determine a location of various facial features within image 800 of the user. After the various facial features (e.g., nose 810, mouth 812, etc.) are determined, Equation 1 may be used to define region of interest 820.

$$ROI = ROI_{previous} + Face_{Area} - [Face_{Coordinates} - 1.5 \times \text{Height}] \quad \text{Equation 1}$$

In Equation 1, ROI is the region of interest, $ROI_{previous}$ may include the entire previous image or a manually inputted region of interest from the previous image, $Face_{Area}$ is the area of face 802 within image 800 of the user, $Face_{Coordinates}$ are the coordinates defining where face 802 is within image 800, and Height is the height of the user. Persons of ordinary skill in the art will recognize that the factor of 1.5 times the Height of the user is merely an approximation of where a user's mouth would be, and any one of these variables may be modified or augmented accordingly.

In another exemplary embodiment, facial features of the user within image 800 are detected. For example, Supervised Descent Method ("SDM") may be used to detect the facial features of the user. SDM, generally, learns a series of parameter updates that, incrementally, minimize the mean of all Nonlinear Least Squares ("NLS") functions in training. SDM is especially useful in scenarios where a Newtonian image alignment method does not work (e.g., where the Hessian matrix for the image is positive definite at the local minimum but may not be elsewhere, and the function is twice differentiable).

In one embodiment, consecutive images captured by camera 602 of user device 150 define the region of interest as the area below the detected facial features using Equation 2.

$$ROI = ROI_{previous} + FF_{Area} - [Face_{Coordinates} - 1.5 \times \text{Height}] \quad \text{Equation 2}$$

In Equation 2, $FF_{Area}$ is defined as [Min(X),Min(Y),Max(X),Max(Y)] for the images captured by camera 602. In one embodiment, $ROI_{previous}$ consists of the entire image 800 or a manually inputted region of interest.

In yet another exemplary embodiment, region of interest 820 of image 800 is detected based on background subtraction techniques. For example, camera 602 of user device 150 may capture a set of consecutive images of a user, such as a video of the user, and extract a user's foreground image/mask. The facial area (e.g., face 802) is extracted, in one embodiment, using skeleton matching and region of interest 820 is defined by Equation 1. Background subtraction, generally, allows for two or more images to be compared so that a certain static portion of the images is removed to highlight a particular portion. For example, a moving image overlaid on a static background may have the static background removed using background subtraction as the static background is consistent from image to image.

In still another exemplary embodiment, region of interest 820 of image 800 is detected based on 3-D modelling. Various types of 3-D modelling include, but are not limited to, matching 3-D models with shape distributions, shape matching by object recognition using shape contexts, and symmetry descriptors for 3-D shape matching, or any other type of 3-D modelling technique, or any combination thereof. For example, one or more 3-D modelling techniques may be used to detect face 802 of image 800 to determine region of interest 820. As another example, the region of interest may be detect by selecting an area of image 800 include a specific body part of the user (e.g., the user's hands). In yet another example, 3-D shape matching may be used to match oral hygiene device 10 to a pre-computed model of an oral hygiene device to determine region of interest 820 by analyzing where the oral hygiene device 10 is within image 800.

In yet still another exemplary embodiment, detection of the region of interest 820 is performed by extraction of physical landmarks on the user and/or oral hygiene device 10. In one embodiment, certain color, edge, texture, or other indicia may be used to specify where region of interest 820 should be. For example, oral hygiene device 10 may have housing 18 shaded red. In this particular scenario, user device 150 may analyze images captured by camera 602 and highlight the motion of any object that is red, thereby tracking oral hygiene device 10. In another embodiment, light-based markers, such as LEDs, are used to specify region of interest 820. For example, oral hygiene device 10 may include one or more infrared LEDs that may be recognized by user device 150 to determine region of interest 820.

Persons of ordinary skill in the art will recognize that any of the aforementioned techniques for determining region of interest 820 within image 800 of the user may be used, or any additional technique or method may be used, and the exemplary embodiments are not to be construed as limiting. Furthermore, one or more of the aforementioned techniques may also be used to determine brushing motion of the user after region of interest 820 is determined or at a substantially same time as region of interest 820 is determined. A more detailed explanation of one or more of the aforementioned techniques will also be described below and in the foregoing figures.

Figure 9A:
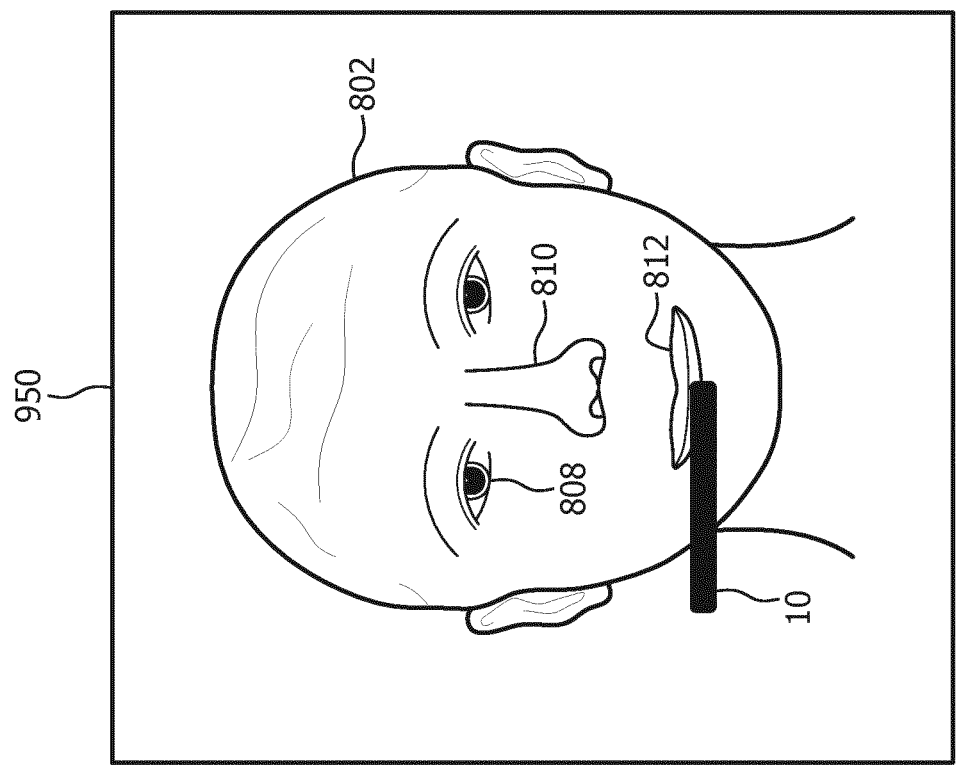
FIGS. 9A and 9B are illustrative diagrams describing a change in a location of a device 10 in accordance with various embodiments.
Figure 9B:
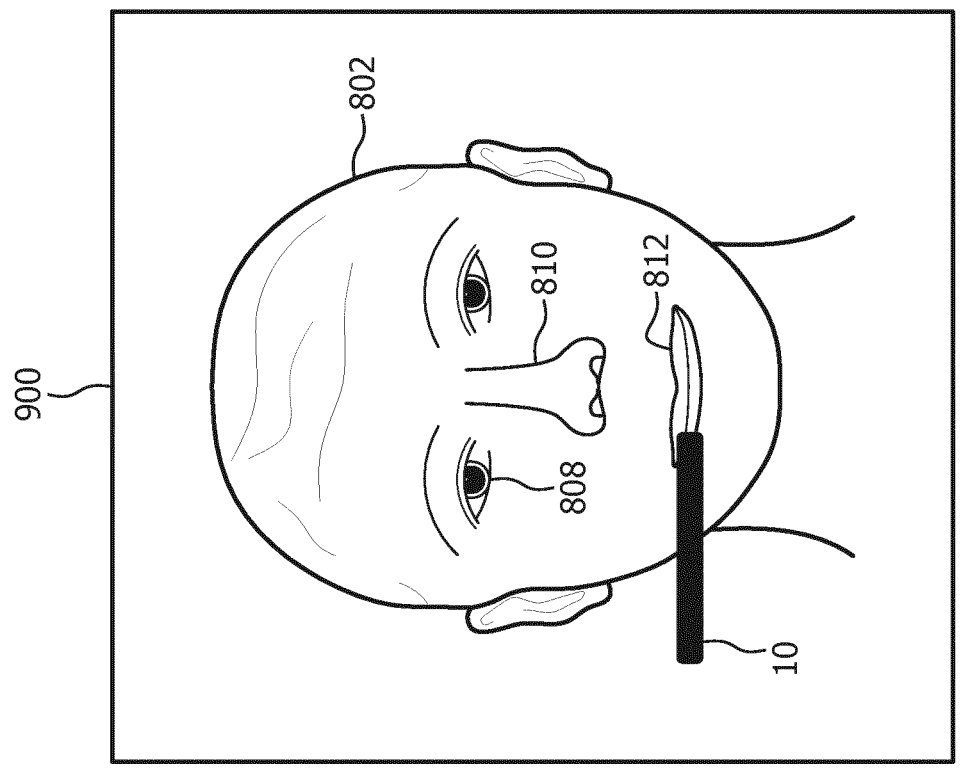

FIGS. 9A and 9B are illustrative diagrams describing a change in a location of a user device, such as oral hygiene device 10 in accordance with various embodiments. A first image 900 of a user, such as the user, includes, in one embodiment, the user's face 802, eyes 808, nose 810, and mouth 812. In addition, first image 900 includes a user device which, in one exemplary embodiment, corresponds to oral hygiene device 10. As a user brushes their teeth, a camera, such as camera 602, captures a new location of oral hygiene device 10 in a second image 950. Oral hygiene device 10 in second image 950 is at a different position than it was in first image 900 with respect to the user. In one embodiment, first and second images 900 and 950 are two individual images captured by camera 602; however first and second images 900 and 950 may also be consecutive images obtained via a video captured by camera 602.

Figure 10:
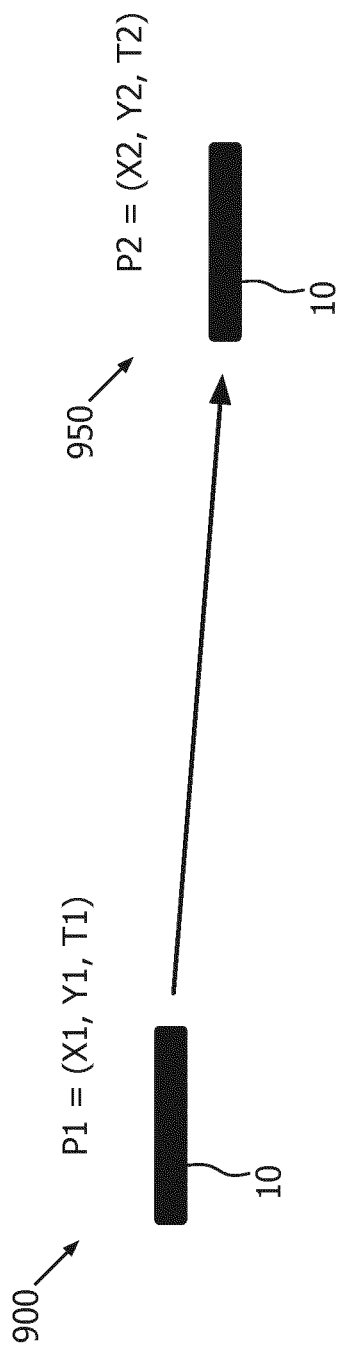
FIG. 10 is an illustrative diagram describing a change in a location of device 10 based on a change in pixel position and frame in accordance with various embodiments.

FIG. 10 is an illustrative diagram describing a change in a location of an oral hygiene device 10 based on a change in pixel position and frame in accordance with various embodiments. In the illustrative embodiment, oral hygiene device 10 from first image 900 of FIG. 9A has an initial pixel position P1, which has a two-dimensional first pixel array position (X1, Y1) and an first time when first image 900 was captured T1, oral hygiene device 10, in second image 950, has a second pixel position P2, where the two-dimensional second pixel array position is (X2, Y2) and the second time when second image 950 was captured is T2.

Based on the coordinates (e.g., pixel and time) of oral hygiene device 10 in first image 900 and second image 950, a change in vertical displacement (e.g., ΔY) and a change in horizontal displacement (e.g., ΔX) are able to be determined. Incorporating time change (e.g., ΔT), an approximation on the motion of device 10 is obtainable. Persons of ordinary skill in the art will recognize that the aforementioned is merely an approximation, and various additional factors such as scaling, delay, and resolution, may also affect the motion characteristics of oral hygiene device 10.

FIG. 11 is an illustrative diagram describing a change in a location of oral hygiene device 10 based on a change in a position vector between oral hygiene device 10 and a reference object in accordance with various embodiments. In the illustrative embodiment, a first position vector 904A is determined by processor 102 of user device 150 that signifies a distance and/or angle between oral hygiene device 10 and a reference object, such as nose 810 of the user. Persons of ordinary skill in the art will recognize that any other reference object may be used including, but not limited to, eyes 808, mouth 812, neck 804, torso 806, or any other feature of the user or background, or any combination thereof.

First position vector 904A, in one embodiment, includes information regarding the positioning of oral hygiene device 10 with respect to nose 810 of the user in first image 900. In second image 950, the position of oral hygiene device 10 has changed, and information regarding the new position of oral hygiene device 10 with respect to nose 810 of the user is included in a second position vector 904B. Each of position vectors 904A and 904B are analyzed by user device 150 and a relative motion of oral hygiene device 10 is determined based on the change in position and timing of the change of position vectors 904A and 904B. Various techniques may be used to estimate the motion between consecutive images 900 and 950 using position vectors, such as position vectors 904A and 904B, including, but not limited to, 3DRS and Optical Flow. Persons of ordinary skill in the art will recognize that any motion extraction technique may be used, however, and the aforementioned are merely exemplary.

FIG. 12 is an illustrative diagram describing a change in a location of oral hygiene device 10 based on a change in a center of gravity of a captured image in accordance with various embodiments. In one exemplary embodiment, motion extraction is performed using absolute frame differencing techniques. For example, a binary difference image ImDiff is computed using Equation 3:

$$\text{ImDiff} = \text{abs}(\text{ImCurrent} - \text{ImPrevious}) > \text{Threshold} \quad \text{Equation 3}$$

In Equation 3, ImCurrent corresponds to the current image and ImPrevious corresponds to a previous image. For example, ImCurrent may correspond to image 950 of FIG. 9B captured by camera 602 of user device 150, whereas ImPrevious may correspond to image 900 of FIG. 9A. The difference between ImCurrent and ImPrevious is taken as the absolute value. Furthermore, in Equation 3, Threshold corresponds to a variable that may be set by the user operating user device 150 or it may be predefined by user device 150. For example, Threshold may correspond to an amount of noise associated with camera 602 and/or in the background environment.

In one embodiment, the difference between ImCurrent and ImPrevious from Equation 3 is projected along the x- and y-axis of the image plane causing two signals, ProjX and ProjY, to be formed. ProjX, in one embodiment, is defined as being the sum of ImDiff along the y-image axis for all values, whereas ProjY is defined as being the sum of ImDiff along the x-image axis for all values. The maximum value for both ProjX and ProjY is then extracted and, in one embodiment, is used as a "center of gravity" of motion. For example, a first center of gravity 906A may be represented a center of gravity between oral hygiene device 10 and nose 810 within image 900, whereas a second center of gravity 906B may represent a center of gravity between oral hygiene device 10 and nose 810 within image 950. In one embodiment, each center of gravity 906A and 906B are computed based on the ImDiff between that particular image and its previous image. Thus, center of gravity 906B, for example, may be calculated based on the maximum value of both ProjX and ProjY for images 900 and 950. In one embodiment, the difference between consecutive centers of gravity is used to determine the motion of oral hygiene device 10. For example, the difference between centers of gravity 906A and 906B may be used to determine the motion of oral hygiene device 10.

In response to extracting motion characteristics, an analysis is performed, in one exemplary embodiment, of the user's motion. By analyzing and characterizing the user's motion, the raw motion signals (e.g., data acquired via one or more of camera 602 and/or sensor(s) 32) may be transformed into various motion features, such as motion frequency, motion amplitude, and/or motion trajectory.

In one embodiment, analysis is performed by pre-processing of the acquired data. For example, various data reduction techniques may be employed to emphasize information within the acquired data corresponding to motion of the user device (e.g., oral hygiene device 10), and this information may be combined into a single, new motion component. Various data reduction techniques include, but are not limited to, Principle Component Analysis ("PCA"), Independent Component Analysis ("ICA"), application of a low/high band-pass filter, or any other data reduction technique, or any combination thereof. For example, a low band-pass filter with a 4 Hz cutoff may be used to remove unwanted high-frequency data.

In another embodiment, the analysis includes performing a frequency characterization. Motion frequency, in one embodiment, is extracted by using a Fourier analysis to find dominant motion frequency via maximum amplitude detection. For example, motion components may be windowed using a Hanning window, and then sent to a FFT, where the dominant frequencies may be extracted by the index of the maximal frequency amplitude. In one embodiment, frequency characterization includes obtaining motion frequency from the acquired data by extracting extrema (e.g., minima and/or maxima), or the number of zero crossings, from the motion components. Furthermore, as previously discussed, amplitude characterization, in one embodiment, is performed using any suitable technique.

In one exemplary embodiment, no data reduction techniques are needed. Here, the motion characteristics (e.g., amplitude characteristics and/or frequency characteristics), are obtained using one or more additional techniques. For example, the x-direction and/or y-direction characteristics of the motion may be combined. As another example, a linear combination of the x-direction and/or y-direction characteristics of the motion may be used. In yet another example, characteristics corresponding to the strongest frequency component with respect to the amplitude component may be used. In still yet another example, characteristics corresponding to the frequency component that is closest to, or furthest from, the targeted frequency component may be used. Persons of ordinary skill in the art will recognize that the use of "x-direction" and "y-direction" is merely illustrative, and any two directions may be used instead (e.g., x- and y-direction, x- and z-direction, y- and z-direction). Furthermore, persons of ordinary skill in the art will recognize that the targeted frequency and/or strongest frequency component may correspond to any frequency component within the frequency spectrum of the system, and may be chosen prior to implementation and/or varied while performing data analysis.

FIG. 13 is an illustrative diagram of various user interfaces in accordance with various embodiments, displaying various graphics including feedback provided to the user operating oral hygiene device 10, or user device 150 For example, if it is determined that the user is brushing their teeth too quickly, display 604 of user device 150 may present user feedback message 1002. As another example, if it is determined that the user is brushing their teeth too slow, display 604 of user device 150 may present user message 1004 advising the user to speed up. As yet another example, if it is determined that the user is correctly brushing their teeth, then display 604 of user device 150 may present feedback message 1006. As still yet another example, if it is determined that the user is brushing a portion of their teeth that was already brushed, or they are brushing a certain area for too long a period of time, display 604 of user device 150 may present user a feedback message 1008 advising the user to change the position of their brushing.

FIG. 14 is an illustrative flowchart of a process 1100 in accordance with various embodiments. Process 1100 begins at step 1102. At step 1102, data is acquired from one or more cameras located on a user device. For example, camera 602 of user device 150 may capture one or more images and/or videos of a user brushing his/her teeth with oral hygiene device 10. As another example, the data may be acquired using a CMOS or CDD image sensor, as well as, or in addition to, a 3D camera system. Furthermore, in one embodiment, the acquired data includes data obtained from one or more captured images/videos and one or more sensors, such as sensor(s) 32 (e.g., a Hall Effect sensor, a force sensor, and/or an accelerometer) of oral hygiene device 10. For example, user device 150 may capture video of the user using oral hygiene device 10 while also obtaining data from sensor(s) 32.

The acquisition rate of camera 602, in one embodiment, enables relevant motion information to be extracted. For example, motion frequency and/or motion amplitude are extractable from the images captured by camera 602. In one embodiment, the acquisition rate of camera 602 is set to be at least twice the expected maximum motion frequency. For example, if the expected motion frequency is 10 Hz, the acquisition rate will be 20 Hz.

In one exemplary embodiment, an additional step (not shown) of pre-processing the acquired data occurs. This optional step may be substantially similar to steps 504 of process 500. For example, pre-processing of the acquired data may downscale the image by a factor of four (4) to reduce relatively large images captured by camera 602.

In another exemplary embodiment, video channel reduction may occur for video images captured by camera 602 of user device 150. For example, red, green, and blue channels of the captured video may be converted into a single luminance channel using Equation 4:

$$Y=0.299R+0.587G+0.114B \quad \text{Equation 4}$$

In Equation 4, Y is the single luminance channel, R is the red channel, G is the green channel, and B is the blue channel. Persons of ordinary skill in the art will recognize that the coefficients for each of the red, green, and blue channel may be modified accordingly depending on the desired settings, and the use of the coefficients in Equation 4 are merely exemplary.

As another example, any input channel of the video captured by camera 602 may be combined using any linear or non-linear combination of the input channels. As still yet another other example, only one video channel, such as a green video channel, may be used. In this particular scenario, the green video channel may be used as it typically includes most of the video signal's energy.

At step 1104, a region of interest is determined. The region of interest is an area or portion of an image of a user that an appropriate motion analysis will target. For example, a user brushing his/her teeth will have region of interest 820 corresponding to an area surrounding and including his/her mouth. For different activities, such as shaving, hair maintenance, flossing, etc., region of interest 820 may change accordingly to include portion(s) of the user's image that include the intended areas where the motion will occur.

Various techniques may be used to determine the region of interest. For example, the region of interest may be predefined by the user and/or the user device, or the region of interest may be selected by the user. In one embodiment, the region of interest is determined automatically based on feature detection. For example, a user's face and chest may be detected using a Viola-Jones face detector or SMD in conjunction with Equation 2. As another example, background subtraction techniques may be used to determine the region of interest, as well as 3-D modelling, and/or physical marker extraction.

At step 1106, the motion of the device is extracted using the region of interest as determined in step 1104. The extraction of the motion of the device may be performed using a variety of techniques. In one embodiment, motion estimation techniques are used to extract the motion. For example, motion vectors are extracted using motion estimation between consecutive images (e.g., using 3DRS and/or Optical Flow techniques). In one embodiment, object tracking is used to extract the motion. For example, the motion is extracted by tracking a real or virtual object (e.g., oral hygiene device 10), or the relative distance between an object and a landmark (e.g., a vector between oral hygiene device 10 and nose 810 of the user). In yet another embodiment, absolute frame differencing is used to extract the motion. Here, a binary difference image between a first image and a second image is computed, and then a maximum value along each axis of the image is determined and used as a center of gravity for the motion. The various centers of gravity are then used in consecutive images to determine the motion.

At step 1108, the extracted motion is analyzed and decomposed into various components, such as motion frequency, motion amplitude, and/or motion trajectory. In one embodiment, pre-processing is used to reduce the data. For example, a PCA, ICA, or a band-pass filter may be applied to the data to remove irrelevant or unneeded information. In one embodiment, frequency characterization is performed to extract motion frequency. For example, motion frequency may be extracted using Fourier analysis to detect a dominate motion frequency and/or by extracting extremas or zero crossings in the motion components. In one embodiment, amplitude characterization is performed to extract motion amplitude. For example, the distance between consecutive extremas, a dominate frequency in the Fourier representation, and/or an envelope of the motion components may be used to extract motion amplitude.

At step 1110, feedback is provided to the user based on the analysis performed at step 1108. In one embodiment, the motion characteristics are compared to a targeted motion stored on the user device. For example, a predefined targeted motion of a user brushing their teeth may be stored in storage 1044 or memory 106 on user device 150. After motion of the user device (e.g., oral hygiene device 10, 10) is extracted, it may be analyzed by comparing it to the predefined target motion. The results of this analysis are the capable of being presented to the user on display 604 of user device 150 so that the user is able to modify their motion to conform with the predefined targeted motion. For example, display 604 may present user interfaces 1002, 1004, 1006 or 1008 of FIG. 11, or user interfaces 200, 300, 300', and/or 400.

In one embodiment, the motion characteristics are used to compute a score presented to the user either in real-time or after the motion is performed. For example, as seen in FIG. 4, user interface 400 includes various scores of a user for brushing sessions. The scores are computed and capable of being presented to the user so that they are able to see days or times when their brushing was good or bad. As another example, a user may be presented with user interfaces 300 or 300', which may allow a user to see in real-time how well they are adhering to target brushing window 310. If their brushing is too low (e.g., user interface 300) the user may modify their brushing to increase pressure and/or frequency, whereas if their brushing is too great (e.g., user interface 300'), the user may modify their brushing to decrease pressure or frequency.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for enhancing a user's efficiency while operating an oral hygiene device, the method comprising:
    capturing at least two images from an image capturing component;
    determining a region of interest for operating the oral hygiene device based on the captured at least two images, wherein the region of interest is predefined in the memory of the user device and selected manually by the user, wherein the user manually selects a sub-region of an image to identify the region of interest;
    extracting, based on the determined region of interest, characteristics corresponding to a motion of the oral hygiene device operated by the user;
    analyzing the extracted characteristics corresponding to the motion of the oral hygiene device operated by the user to determine a quality of the motion of the oral hygiene device; and
    providing feedback to the user regarding the determined quality of the motion of the oral hygiene device.

2. The method of claim 1, wherein:
    the oral hygiene device comprises a housing portion and an attachment assembly portion;
    the housing portion is located at a first end of the oral hygiene device and the attachment assembly portion is located at a second end of the oral hygiene device; and
    the image capturing component is located on the oral hygiene device at one of the first end and the second.

3. The method of claim 1, wherein the image capturing component is located on a user device capable of capturing images of the oral hygiene device while being operated by the user.

4. The method of claim 1, further comprising:
    performing data reduction to the at least two captured images prior to the region of interest being determined.

5. The method of claim 1, wherein determining further comprises:
    detecting at least one physical landmark of the user.

6. The method of claim 5, wherein extracting further comprises:
    tracking the motion of the oral hygiene device using the detected at least one physical landmark of the user.

7. The method of claim 5, wherein:
    the at least one physical landmark comprises at least one of the user's nose, the user's ears, the user's eyes, the user's palate, the user's torso, and the user's tongue.

8. The method of claim 1, wherein the oral hygiene device further comprises at least one accelerometer.

9. The method of claim 1, wherein the provided feedback comprises at least one of: an audible sound, a visual signal, and a haptic response.

10. A user device for aiding a user in enhancing an effectiveness for operating an oral hygiene device, the user device comprising:
    at least one image capturing component;
    a display screen having a user interface, wherein the user manually selects a sub-region of an image to identify a region of interest;
    communications circuitry;
    memory; and at least one processor operative to:

capture, using the at least one image capturing component, at least two images of the user operating the oral hygiene device;

extract, in response to detecting that the user is operating the oral hygiene device in the region of interest, motion information of the oral hygiene device from the captured at least two images, wherein the region of interest is identified, using the user device, based on manual selection by the user;

analyze the extracted motion information of the oral hygiene device operated by the user by comparing the extracted motion information to a predefined targeted motion for the oral hygiene device stored in the memory on the user device to determine a quality of the extracted motion information of the oral hygiene device; and provide feedback to the user operating the oral hygiene device, wherein the provided feedback comprises the determined quality of the extracted motion information.

11. The user device of claim 10, wherein: the provided feedback comprises visual feedback presented within a user interface displayed on the display screen of the user device.

12. The user device of claim 10, wherein the at least one processor is further operative to:

apply, prior to the analysis, a low pass filter to the extracted motion information, wherein the low pass filter has a 4 Hz cutoff.

13. The user device of claim 10, wherein the at least two captured images comprise video, the at least one processor is further operative to at least one of:

convert the video into a single luminance channel using a combination of red, green, and blue video channels for the analysis; and select one of the red, green, and blue video channels to convert the video into the single luminance channel for the analysis.

14. The user device of claim 10, wherein the at least two captured images comprises a plurality of captured images, the at least one processor is further operative to:

perform an absolute frame difference analysis on the plurality of captured images to determine differences in consecutive centers of gravity of each captured image of the plurality of captured images.

\* \* \* \* \*